United States Patent [19]

Gonick et al.

[11] Patent Number: 5,426,122

[45] Date of Patent: *Jun. 20, 1995

[54] METHODS FOR REDUCING BLOOD PRESSURE WITH DIMERCAPTOSUCCINIC ACID (DMSA)

[75] Inventors: Harvey C. Gonick; Farhad Khalil-Manesh, both of Los Angeles, Calif.; Elmar W. J. Weiler, Saarland, Germany

[73] Assignee: Cedars-Sinai Medical Center, Los Angeles, Calif.

[ * ] Notice: The portion of the term of this patent subsequent to Oct. 9, 2007 has been disclaimed.

[21] Appl. No.: 990,753

[22] Filed: Dec. 15, 1992

Related U.S. Application Data

[63] Continuation-in-part of Ser. No. 553,999, Jul. 16, 1990, abandoned, and a continuation-in-part of Ser. No. 325,297, Mar. 17, 1989, Pat. No. 4,962,127.

[51] Int. Cl.⁶ .......................................... A61K 31/185
[52] U.S. Cl. .................................................... 514/578
[58] Field of Search ........................................ 514/578

[56] References Cited

U.S. PATENT DOCUMENTS 4,962,127  10/1990  Gonick et al. ...................... 514/578

OTHER PUBLICATIONS

Aposhian, H. V. "DMSA & DMPS—Water Soluble Antidotes for Heavy Metal Poisoning," *Ann. Rev. Pharmacol. Toxicol.*, 23:193–215 (1983).

Cantilena, L. R. et al., "The Effect of Repeated Administration of Several Chelators on the Distribution and Excretion of Cadmium", *Tox. Appl. Pharm.*, 66:361–67 (1982).

Cloix, J. F. et al., "Plasma Protein Changes in Primary Hypertension in Humans and Rats", *Hypertension*, 5:128–34 (1983).

Domingo, J. L. et al., "Acute Aluminum Intoxication: A Study of the Efficacy of Several Antidotal Treatments in Mice", *Res. Com. Chem. Pathol. Pharm.*, 53:93–104 (1986).

Domingo, J. L. et al., "Developmental Toxicity of Subcutaneously Administered meso-2,3 Dimercaptosuccinic Acid in Mice", *Fund. Appl. Tox.*, 11:715–22 (1988).

Gonick, H. C. et al., "Comparison of Low Molecular Weight Plasma and Urine Na-K-ATPase Inhibitors/Hypertensive Factors " (1973).

Handmaker, H. et al., "Clinical Experience with $^{99m}$Tc-DMSA (Dimercaptosuccinic Acid), A New Renal-Imaging Agent", *J. Nucl. Med.*, 16:28–32 (1973).

Hoefnagel, C. A. et al., "New Radionuclide Tracers for the Diagnosis and Therapy of Medullary Thyroid Carcinoma", *Clin. Nucl. Med.*, 13:159–65 (1988).

Ignarro, L. J., "Biosynthesis and Metabolism of Endothelium-Derived Nitric Oxide", *Ann. Rev. Pharmacol. Toxicol.*, 30:535–60 (1990).

John, A. et al., "Identification of a So-far Not Characterized Human Serum Protein Associated With Essential Hypertension", *Electrophoresis*, 6:292–95 (1985).

Kondo, K. et al., "Simultaneous Measurement of Endothelium-Derived Relaxing Factor By Bioassay and Guanylate Cyclase Stimulation", *Br. J. Pharmacol.*, 98:630–36 (1989).

Liang Yu-i et al., "The Antidotal Effects of Sodium Dimercaptosuccinate and Bal-Glucoside Against Tartar Emetic", *Acta Physiol. Sin.*, 21:24–32 (1957).

(List continued on next page.)

*Primary Examiner*—Raymond Henley, III
*Assistant Examiner*—T. J. Criares
*Attorney, Agent, or Firm*—Lyon & Lyon

[57] ABSTRACT

Methods for treatment of humans and other animals with dimercaptosuccinic acid (DMSA). DMSA is administered to reduce levels of silicon in blood and tissue, reduce blood pressure, improve kidney function, prevent or retard the progression of chronic renal failure, treat the accumulation of silicon in advanced kidney disease, decrease accumulation of reactive oxygen metabolites, increase superoxide dismutase activity, and/or prevent the onset or improve the current status of senile dementia or Alzheimer's disease.

7 Claims, 11 Drawing Sheets

OTHER PUBLICATIONS

Llobet, J. M. et al., "Comparison of the Effectiveness of Several Chelators After Single Administration on the Toxicity, Excretion and Distribution of Cobalt", *Arch. Toxicol.*, 58:278–81 (1986).

Llobet, J. M. et al., "Antidotes for Zinc Intoxication in Mice", *Arch Toxicol.*, 61:321–23 (1988).

Lüscher, T. F., "Imbalance of Endothelium–derived Relaxing and Contracting Factors", *Am. J. Hypertension*, 3:317–30 (1990).

Lüscher, T. F. et al., "Endothelium–derived Relaxing and Contracting Factors: Perspectives in Nephrology", *Kidney Int'l.*, 39:575–90 (1991).

Lyons, K. P. et al., "Mycardial Infarct Imaging in Patients with Technetium–99m 2,3–Dimercaptosuccinic Acid—Superiority of Technetium–99m Pyrophospahte", *Clin. Nucl. Med.*, 12:514–18 (1987).

Maiorino, R. M. et al., "Determination and Metabolism of Dithiol–Chelating Agents: Electrolytic and Chemical Reduction of Oxidized Dithiols in Urine", *Anal. Biochem.*, 160:217–26 (1987).

Morich, F. J. et al., "Characteristic Changes of Plasma Proteins in the Dahl Hypertensive Rat Strain (DS) During the Development of Hypertension", *J. Hypertension*, 3:249–53 (1985).

Nardi, R. et al., "Characteristic Variation in the Plasma Proteins in Essential Hypertension", *Clinical & Experimental Hypertension*, 3:775–81 (1981).

Shainkin–Kestenbaum, R. et al., "Inhibition of Superoxide Dismutase Activity by Silicon", *J. Trace Elem. Electrolytes Health Dis.*, 4:97–99 (1990).

Van de Voorde, A. et al., "Isolation of a Plasma Protein Observed in Patients with Essential Hypertension", *Biochem. Biophys. Res. Com.*, 111:1015–21 (1983).

Watkinson, J. C. et al., "An Evaluation of the Uptake of Technetium–99m(v) Dimercaptosuccinic Acid in Patients with Squamous Carcinoma of the Head and Neck", *Clin. Otolaryngol.*, 12:405–11 (1987).

Webb, R. C. et al., "In Vivo and In Vitro Effects of Lead on Vascular Reactivity in Rats", *Am. Physiol. Soc.*, H211–H216 (1981).

Weber, M. A. et al., "Effects of a Human–Derived Sodium Transport Inhibitor on In Vitro Vascular Reactivity", *Am. J. Hypertension*, 2:754–61 (1989).

METHODS FOR REDUCING BLOOD PRESSURE WITH DIMERCAPTOSUCCINIC ACID (DMSA)

This application is a continuation-in-part of application Ser. No. 553,999, filed on Jul. 16, 1990, now abandoned and a continuation of application Ser. No. 325,297, filed on Mar. 17, 1989 and now issued as U.S. Pat. No. 4,962,127, and whose entire disclosures are incorporated herein by reference.

FIELD OF THE INVENTION

This invention relates generally to methods for treatment of patients by administering dimercaptosuccinic acid (DMSA). More particularly, this invention relates to methods for treatment of patients by administering DMSA to reduce silicon levels in human blood and tissue, to reduce blood pressure, improve kidney function, prevent or retard the progression of chronic renal failure, treat the accumulation of silicon in advanced kidney disease, decrease accumulation of reactive oxygen metabolites (possibly through increased activity of superoxide dismutase), and/or prevent the onset or improve the current status of senile dementia and Alzheimer's Disease.

BACKGROUND OF THE INVENTION

Silicon, next to oxygen, is the most prevalent element on earth, and is the most abundant mineral in the earth's crust. It occurs in nature as silica (silicon dioxide—$SiO_2$) or corresponding silicic acids. Silicon is present in plants, and is widespread in foodstuffs, particularly monocotyledons such as grain, in clay (aluminum silicate), in sand, and in glass. In medicine, silicon is used therapeutically as magnesium trisilicate, and as organic compounds used as defoaming agents. Silicones (organosiloxanes) are used in various cosmetic surgical implant procedures. Due most probably to dietary intake, at least small amounts of silicon may be found in most animal tissues and fluids (Scot. Med. J. 27:17-19 (1982)).

Silicon is a trace element, comprising less than 0.01% of the human body. Silicon has been demonstrated as an essential element, i.e., one that is required for maintenance of life, and when deficient consistently results in an impairment of a function from optimal to suboptimal (Science 213:1332 (1981)).

Proof of the essentiality of silicon was independently established by two investigators. Carlisle established a silicon deficiency state incompatible with normal growth in chicks (Science 178:619 (1972)), and Schwartz and Milne showed similar results with rats (Nature, 239:33 (1972)). Using comparable methods, both studies showed that the animals responded to supplementation with sodium metasilicate with a 30 to 50 percent stimulation in growth. Subsequent examination of the animals raised on silicon-deficient diets revealed depressed bone growth and severe bone deformities, particularly of the skull.

Although silicon has been known as a regular constituent of biological materials since the beginning of the century, little is known about its metabolism. It is known that silicon specifically concentrates in the mitochondria of osteoblasts, and that it plays a role in bone and cartilage formation (Science 213:1332 (1981)). In addition, since silicon is present in high concentrations in collagen, it has been suggested that silicon plays a role in cross-linking connective tissues at the level of mucopolysaccharides (Fed. Proc, 33:1748 (1974)). It has therefore been postulated that apart from bone formation, silicon participates in growth and maintenance of connective tissue, as in embryonic development and wound healing, and in regulation of ions, metabolites and water in connective tissue. (Fed. Proc. 33:1758-1766 (1974)).

Silicon in foods and beverages is readily absorbed across the intestinal wall. Studies have shown that there is a narrow range of silicon concentration in the serum of healthy adults, and with the exception of urine, the concentrations of silicon in all other body fluids is similar to that of normal serum. Higher and wider ranges of silicon levels in the urine show that the kidney is the main excretory organ for silicon absorbed from the alimentary canal (Scot. Med. J. 27:17-19 (1982)).

The level of silicon in the blood and tissues has been shown to be affected by age, as well as by sex, castration, adrenalectomy and thyroidectomy (Ann. Endocrinol. 32:397 (1971)). The silicon content of the aorta, skin and thymus in the rabbit, rat, chicken and pig was found to significantly decline with age, whereas other tissues such as the heart, kidney, muscle and tendon show little or no change (Fed. Proc. 33:1758-1766 (1974)). In addition, the silicon content of the dermis of human skin has been shown to diminish with age (J. Biol. Chem. 75:789-794 (1927)). In contrast, Leslie et al. showed an increase in rat brain, liver, spleen, lung and femur silicon with age (Proc. Soc. Exptl. Bio. Med. 110:218 (1962)). And Kworning et al. described elevated silicon deposition in the human aorta wall during aging (J. Geront. 5:23-25 (1960)). In addition, it has been demonstreated that silicon was elevated in the aorta with focal atherosclerosis, as well as in the atherosclerotic focus itself (Folia Morph. 25:353-356 (1977)). Further, it has been reported that with advancing age, the $SiO_2$ level of human peribronchial lymph glands gradually increases even in those who have no history of exposure to dust (J. Pathol. 51:269-275 (1940)). Our own work, moreover, has demonstrated an increase of kidney silicon levels in normal rats with aging.

Although silicon is an essential trace element for human growth and is necessary for bone formation, silicon intoxication has been shown to cause various diseases. In addition to cases of acute toxicity, there is justifiable suspicion that the pathogenesis of some chronic diseases may be related to prolonged exposure to concentrations of toxins insufficient to produce conspicuous manifestations (J. Chron. Dis. 27:135-161 (1974)). For example, a substantial portion of patients with terminal renal failure have no clearly definable etiology of their renal disease. It may be speculated therefore that some renal disease may be associated with chronic exposure to certain toxins, including silicon.

Much information is known about the toxic effects of silicon in the lung. Varying amounts of silica normally enter the respiratory tract across the lung barrier as silicic acid and are eventually eliminated. Prolonged inhalation and accumulation of fine particulate silica in the lung, however, produces a pulmonary inflammatory response, granuloma formation and chronic fibrosis (silicosis) (Prin. Int. Med., 9th Ed., Isselbacher et al. (eds), McGraw-Hill Book Co., N.Y. 1980). In silicosis, the injury seems to be related to both the crystal structure of the silicon and the host response. Workers in stone quarries, or in other industries where sand or other silicate dusts are prevalent, are prone to contract this disease.

It is commonly believed that ingested silicates are both inert and nonabsorbable, but there has long been a suspicion that silicates are nephrotoxic in humans (*Scot. Med. J.* 27:10-17 (1982)). In 1922, Gye and Purdy investigated the toxicity of parenterally administered colloidal silica in rabbits which resulted in interstitial nephritis, hepatic fibrosis and splenomegaly within a period of weeks to several months (*Br. J. Exp. Path.* 3:75-85 (1922)). These findings were later confirmed by Schepers et al. (*AMA Arch. Industr. Hlth.* 15:599 (1957)). In 1970, Newberne and Wilson showed that oral administration of certain silicates produced significant renal tubular damage and chronic interstitial inflammation in dogs (*Proc. Nat. Acad. Sci.* 5:872-875 (1970)). And in 1982, Dobbie and Smith showed that oral ingestion of magnesium trisilicate resulted in renal damage in guinea pigs in four months (*Scot, Med. J.* 27:10 (1982)). Recently, Shainkin-Kestenbaum et al. showed in in vivo studies that silicon in concentrations similar to those found in the serum of uremic patients inhibited superoxide dismutase, an enzyme that destroys oxygen free radicals which can damage cells (*J. Trace Elem. Electrolytes Health Dis.* 4:97 (1990)).

In humans, chronic exposure to silica has been associated with mild renal functional abnormalities and minor histologic changes in the kidneys. Bolton et al. reported four patients with a history of intense silica exposure and rapidly progressive renal failure, and concluded that silicon appeared to be responsible for the nephrotoxic changes (*Am. J. Med.* 71:823 (1981)). Silicon has also been shown to have a direct dose-dependent toxic effect on the kidney (*J. Pathol.* 103:35-40 (1970)), and silicon particles are cytotoxic, as shown by studies demonstrating damage to macrophages ingesting silicon (*Am. Rev. Respir. Dis.* 113:643-665 (1976)).

Since it is known that the principal organ of silicon elimination is the kidney, it is not surprising that an increase in plasma silicon levels (*Biomedicine* 33:228-230 (1980)), as well as an increase in certain tissue silicon levels, have been reported in studies of patients suffering from chronic renal failure and in patients on hemodialysis. (*J. Chron. Dis.* 27:135-161 (1974)). The accumulation of increased quantities of silicon in renal failure results from its decreased renal clearance (*J. Chron. Dis.* 27:135-161 (1974)). The high serum silicon levels demonstrated in hemodialysis patients have been associated with osteitis fibrosa (*Xth Intl. Cong. of Nephr.*, Jun. 26-31, 1987), and elevated cerebral spinal fluid (CSF) silicon levels have been observed in patients with chronic renal insufficiency where CSF silicon levels increased as renal function declined (*Neurology:* 86-789 (1983)). It has been hypothesized, therefore, that since silicon is nephrotoxic and accumulates in blood and body tissues of patients with renal failure, silicon may contribute to the steady progression of renal failure once initiated. (Id.)

In addition to silicon, aluminum has been found to accumulate in advanced kidney disease patients on chronic hemodialysis. Currently, the most effective means of increased removal of aluminum during hemodialysis is by chelation with desferrioxamine (DFO) (*Clin. Nephr.* 24:594-597 (1985)). At the end of a dialysis treatment, the chelator is administered to the patient, whereupon at the next dialysis session, the aluminum-DFO complex is removed. Various dialysis related modalities may be used to remove the aluminum-DFO complex including hemodialysis, peritoneal dialysis, hemofiltration or charcoal (or resin) hemoperfusion (*Kid. Int'l* 33 suppl. 24:5-171 (1988)). Known side effects of DFO treatment include anaphylactic reactions, abdominal pain, posterior cataracts, visual impairments and predisposition to development of fungal infections. DFO has not yet been investigated for its ability to form stable complexes with silicon (*Neph.* 24 at Table 1, p. 595). A need continues to exist, therefore, for a chelator that would help promote the removal of silicon accumulation in patients with advanced kidney disease on chronic hemodialysis.

Impaired renal function can cause secondary hypertension. (*Clin. and Exp. Hypertension* 3(4):775 (1981)). Thus, any treatment, including the reduction of silicon, which improves renal function may also reduce some forms of hypertension.

The cause of essential hypertension is unclear, but several laboratories have detected a low molecular weight protein (MW=12,000-15,000) in the plasma of many patients with essential hypertension and in animals with hereditary forms of hypertension (*Hypertension* 5:128 (1983); *Electrophoresis* 6:292 (1985); *J. Hypertension* 3(3):249 (1985); *Biochem. Biophys. Res. Commun.* 111(3):1015 (1983)). This protein has been called the "hypertension associated protein" or HAP.

Our laboratory has partially purified HAP from plasma of a patient with volume-expansion related hypertension (primary aldosteronism). The semi-purified HAP was shown to have the properties attributable to natriuretic hormone, i.e., to induce natriuresis in a test animal, to inhibit the active transport enzyme, Na-K-ATPase, and to displace $^3$H-ouabain from its binding sites on purified Na-K-ATPase (Weiler, et al., "Characterization of a Volume-Responsive Low Molecular Weight Protein in Human Plasma"). We have also demonstrated that a low molecular weight Na-K-ATPase inhibitor dissociated from HAP can independently induce vasoconstriction and potentiate the vasoconstriction caused by norepinephrine in isolated blood vessels (Gonick, et al., "Comparison of Low Molecular Weight Plasma and Urine Na-K-ATPase Inhibitors/Hypertensive Factors").

Hypertension can occur when the blood vessels constrict. Therefore, one way to reduce blood pressure is to dilate the blood vessels. A hormonal system locally produced in blood vessels is one system which controls dilation and constriction of blood vessels. Endothelium-derived relaxing factor (EDRF), which has been equated to nitric oxide (NO) or closely related compounds, causes vasodilation by activating guanylate cyclase within the vascular smooth muscle. The guanylate cyclase produces cyclic GMP (cGMP), which decreases the intracellular concentration of calcium cations ($Ca^{2+}$), resulting in vasodilation, decreased peripheral vascular resistance, and reduced blood pressure (*Annu. Rev. Pharmacol. Toxicol.* 30:535 (1990); *American J. Hypertension* 3:317 (1990)). Kondo et al. have found that superoxide dismutase increased the basal activity of guanylate cyclase, probably through the removal of superoxide anions ($O_2^-$) (*Br. J. Pharmacol.* 98:630 (1989)). Lüscher et al. noted that superoxide anions destroy EDRF, while the free radial scavenger superoxide dismutase prolongs its half-life, and that the main disorder in atherosclerotic arteries is a decreased release of EDRF (*Kidney Int'l* 39:575 (1991)). Therefore, a compound stimulating EDRF or superoxide dismutase should cause a reduction in blood pressure.

Silicon may also be a neurotoxin. Silicon, together with aluminum, are significantly elevated in Alzheimer's disease in the neurofibrillary tangles, and in senile dementia there is a diffuse increase in silicon levels in the brain (*Science* 208:297-298 (1980)). Nikaido et al. demonstrated that patients with Alzheimer's disease showed a substantial increase of silicon in the cores and rims of the senile plaques. (*Arch. Neurol.* 27:549-554 (1922)).

Meso-2,3-dimercaptosuccinic acid (DMSA) is a water soluble compound analogous to 2,3-dimercaptopropanol (BAL). In contrast to BAL, however, DMSA is less toxic, has greater water solubility, limited lipid solubility, and is effective when given orally (*Fund. Appl. Tox.* 11:715-722 (1988)). DMSA may be administered orally or parenterally. A preferred dosage of DMSA for humans is 10-30 mg/kg daily.

DMSA is available as a white crystalline powder and exists in two forms, the meso form and the DL form. Because meso-DMSA is easier to synthesize and purify, it is more readily available and has been used in most published investigations. Meso-DMSA (m.p. 210°-211° C.) is sparingly soluble and must be titrated to approximately pH 5.5 to go into solution, or dissolved in 5% $NaHCO_3$. The DL form (m.p. 124-125), on the other hand, is readily soluble in distilled water. (*Ann. Rev. Pharmacol. Toxicol.* 23:193-215 (1983)). As used herein, DMSA includes but is not limited to the meso, racemic and D and L isomers, whether derived from isomeric resolution of the racemic form or derived from stereospecific synthesis. DMSA is available from a variety of biochemical specialty firms.

DMSA was originally introduced by Friedheim and DaSilva in 1954 to promote uptake of antimony during schistosomiasis therapy (*J. Pharm. Exp. Therap.* 246:84 (1988)), and was first recognized as an antidote for heavy metal toxicity by Liang et al. in 1957 (*Acta Physiol. Sin.* 21:24-32 (1957)). Since then, DMSA has been shown to remove toxic forms of lead, mercury and arsenic from the body via urinary excretion, presumably by forming water-soluble metal complexes or chelates (*Anal. Biochem.* 160:217-226 (1987)).

DMSA has been shown to have variable success as an antidote for other toxicities. DMSA was reported to be effective at reducing the concentration of aluminum in the liver, spleen and kidney (*Res. Com. Chem. Pathol. Pharm.* 53:93-104 (1986)), reducing the concentration of cobalt in the liver, brain, heart and blood (*Arch. Toxicol.* 58:278-281 (1986)), and as an antagonist for acute oral cadmium chloride intoxication by increasing the urinary elimination of cadmium (*Tox. Appl. Pharm.* 66:361-367 (1982)). DMSA, however, did not increase urinary and fecal excretion of cobalt (*Arch. Toxicol.* 58:278-281 (1986)), and showed lower efficacy than other chelating agents as an antidote for zinc poisoning (*Arch. Toxicol.* 61:321-323 (1988)). (See *Ann. Rev. Pharm. Toxicol.* 23:193-215 (1983) for a review of the success and failure of DMSA in treating toxicities).

DMSA has also been labeled with $^{99}Tc$ for use in renal scanning (*J. Nucl. Med.* 16:28-32 (1973), tumor detection (*Clin. Otalary* 12:405-411 (1987) and *Clin. Nucl. Med.* 13:159-165 (1988)), and for imaging myocardial infarcts (*Nucl. Med.* 12:514-518 (1987)).

DMSA has been reported as an effective and relatively nontoxic agent for treatment of metal poisoning. Other chelating agents have also been used as antidotes for metal toxicities, but these drugs have been shown to have many side effects. BAL is administered by a painful intramuscular injection and can cause nausea, vomiting and severe headache. Calcium disodium ethylenediaminetetraacetic acid ($CaNa_2$ EDTA) must be administered parenterally, either intravenously or intramuscularly. It is painful when given intramuscularly, and when given in excessive dosage, can cause nephrotoxicity. Penicillamine is administered orally but is not as effective as BAL or $CaNa_2$ EDTA. Additionally, it can cause reactions resembling penicillin sensitivity, is potentially nephrotoxic and causes neutropenia (*Clinical Tox.* 25:39-51 (1987)).

To date, there are no known chelating agents effective for silicon removal, as well as no previously demonstrated effects of silicon removal. A need exists, therefore, for a method to remove silicon from the body, thereby improving blood pressure and kidney function, reducing neurological toxicities, and returning silicon to youthful levels.

The entire disclosures of the publications and references referred to above and hereafter in this specification are incorporated herein by reference.

SUMMARY OF THE INVENTION

Human exposure to silicon compounds is widespread, either in food, beverages, drinking water, medicine or the external environment. Many foods and beverages contain naturally occurring plant silicates, and there is an increasing use of silicon compounds in the food manufacturing industries where they are extremely useful in preparation and stabilization. Amorphous silicates are widely used as anticaking agents in manufactured food powders, extracts and condiments. Silicon is present in beverages largely due to the natural silicate content of the materials used in their production, as is the case with some beers made from grains. Silicates are frequently incorporated into medicines such as analgesic powders, mixtures and tablets. Colloidal silicas are used in the pharmaceutical industry as desiccants since they have a large surface area and highly polar silanol surface favorable for water vapor absorption. Silicon present in silicate dusts or sand, and silicon used in the computer industry in semiconducting devices, represent yet other sources of silicon exposure.

Long term silicon ingestion and accumulation, as well as silicon intoxication from industrial sources, creates the potential for nephrotoxicity, neurotoxicity and other disease states. In addition, increased silicon levels in cases of renal failure or hemodialysis may further aggravate these conditions. Since silicon is a known component of scar tissue, elevated silicon levels could contribute to progressive scarring.

Thus, it is the object of the present invention to provide a method of reducing silicon levels in the body.

It is the second object of the invention to provide a method of removing kidney silicon in various types of kidney diseases, thereby retarding progressive renal scarring and failure.

It is another object of the present invention to provide a method for improving blood pressure and returning kidney function to normal levels.

It is another object of the present invention to provide a method for treating accumulation of silicon in advanced kidney disease.

It is another object of the present invention to provide a method of reducing brain silicon levels thereby preventing the onset of dementia and Alzheimer's disease or improving a current diseased status.

It is yet a further objective of the present invention to provide a method for reducing damage to cells caused by reactive oxygen metabolites by reducing accumulation of such metabolites, through one or more mechanisms such as increased activity of superoxide dismutase.

DETAILED DESCRIPTION

Figure 1:
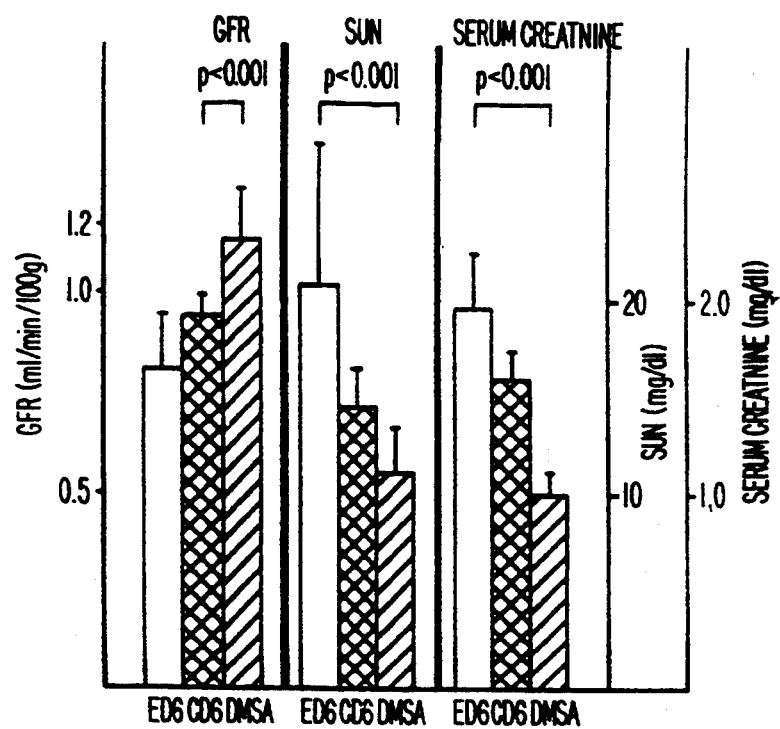
FIG. 1 is a graph showing the effect of DMSA on the Glomerular Filtration Rate (GFR). The DMSA group is compared to normal controls (CD6) and to animals treated with lead for six months, then sacrificed at twelve months (ED6).

In the course of an experiment designed to examine the effect of lead on kidney function and blood pressure, as well as the effect of DMSA on removal of lead, we have unexpectedly found that DMSA reduces kidney silicon to levels seen in young normal control animals and far below the aged normal controls. In addition, DMSA-treated animals had restoration of glomerular filtration rates (GFR) and blood pressure to the same level as young animals, possibly due to reduction in silicon. Although DMSA also reduced kidney lead content, the reduction in lead was less than that seen in lead-treated animals where lead was discontinued at six months (ED6) and where no improvement in GFR or blood pressure was seen. Thus, the reduction in silicon levels and/or the administration of DMSA was more likely to be related to these favorable effects than reduction in lead.

While it appears that reduction in silicon is responsible for the beneficial effects of administration of DMSA, it is possible that other factors, including a reduction in other trace elements, may affect or contribute to the results achieved. For example, Shainkin-Kestenbaum et al. showed that silicon inhibits the enzyme superoxide dismutase (*J. Trace Elem. Electrolytes Health Dis.* 4(2):97 (1990)). Superoxide dismutase reduces the levels of oxygen free radicals (or reactive oxygen metabolites) which can cause cell damage. The lung, brain, kidney and red blood cells contain many compounds which are especially sensitive to oxygen free radical damage, such as phospholipids of brain myelin, lung surfactant, and red blood cells' lipid membranes and hemoglobin. The presence of excessive silicon concentration both induces oxygen free radical formation and suppresses their elimination by inhibition of superoxide dismutase, thereby contributing to severe cell damage. Elevated levels of oxygen free radicals occur in conditions such as renal failure, inflammatory conditions, and in the aging process. Therefore, it appears that DMSA can decrease accumulation of reactive oxygen metabolites and increase activity of superoxide dismutase, and thereby improve such conditions, as well as hypertension, Alzheimer's disease, and senile dementia conditions.

EXAMPLE 1

Rat-Kidney Emission Spectroscopy Results

Male Sprague-Dawley rats were fed beginning at eight weeks of age and sacrificed according to the following schedule:

(1) Controls (C): fed only a semi-purified diet
    C1—sacrificed at one month after initiation of the experiment
    C6—sacrificed at six months
    C12—sacrificed at twelve months
    CD6—sacrificed at 12 months (2) Experimental continuous (EC): fed semi-purified diet and 0.5% lead acetate in drinking water throughout the experiment.
EC1—sacrificed at one month
EC12—sacrificed at twelve months
(3) ED6—Experimental discontinuous: fed semi-purified diet and 0.5% lead acetate in drinking water for six months, no lead in drinking water for the subsequent months; sacrificed at twelve months.
(4) DMSA: fed semi-purified diet and 0.5% lead acetate in drinking water for six months, no lead for the subsequent six months while treated with 0.5% DMSA in drinking water for five days every two months; sacrificed at twelve months.

After sacrifice, kidneys were excised, digested, and analyzed using an emission spectrometer procedure known in the art for determining elements frequently found in biological tissues. Specifically in this study, the sample elements were volatilized and excited in a 12 a D.C. arc. The various element signals were sorted and recorded with an ARL 1.5 m grating spectrometer. The signal data, which were automatically transferred to IBM punched cards, were processed to concentrations in ppm dry weight with an IBM 360-91 computer. The following elements were determined: sodium, potassium, calcium, phosphorus, magnesium, cadmium, zinc, copper, lead, iron, manganese, aluminum, silicon, boron, tin, cobalt, nickel, molybdenum, titanium, chromium, strontium, barium, lithium, silver and vanadium. Results are as shown in Table 1. Only silicon and lead are listed, as the other elements did not show major changes.

TABLE 1

| | TRACE ELEMENTS IN KIDNEY | | | | | | | |
|---|---|---|---|---|---|---|---|---|
| | C1 | C6 | C12 | CD6 | EC1 | EC12 | ED6 | DMSA |
| Si (ppm) | 9.42± 8.64 | 12.32± 6.05 | 98.00± 38.74 | 299.00± 209.74 | 8.31± 14.10 | 137.00± 98.01 | 124.22± 118.89 | 5.31± 8.08 |
| Pb (ppm) | 5.00± 2.96 | 1.96± 1.53 | 1.57± 1.46 | 0.75± 1.39 | 70.33± 23.67 | 291.78± 187.18 | 54.22± 24.94 | 132.29± 127.96 |

EC1 = experimental group (fed 0.5% lead in drinking water); sacrificed at 1 month.
C1 = controls for EC1.
C6 = controls sacrificed at 6 months.
EC12 = experimental group (fed 0.5% lead in drinking water); sacrificed at 12 months.
C12 = controls for EC12.
ED6 = experimental discontinuous group (fed 0.5% lead in drinking water for 6 months, no lead for the subsequent 6 months); sacrificed at 12 months.
CD6 = controls for ED6.
DMSA = DMSA-treated rats (fed 0.5% lead in drinking water for 6 months, no lead for the subsequent 6 months while treated with 0.5% DMSA in drinking water for 5 days every 2 months); sacrificed at 12 months.

As can be seen in Table 1, C12 and CD6 silicon levels increased significantly with age when compared to C1 and C6. The rats fed DMSA, however, showed significantly decreased levels of silicon as compared to the older controls (C12 and CD6) and to experimental animals (EC12 and ED6).

EXAMPLE 2

Determination of GFR

Measurement of the glomerular filtration rate (GFR) provides a sensitive and commonly employed index of overall renal excretory function. GFR can be assessed indirectly by measurement of plasma creatinine or serum urea nitrogen (SUN) levels, and directly by clearance of inulin ($C_{36} H_{62} O_{31}$) or by clearance of various radioactive substances handled by the kidney in the same way as inulin (e.g., iothalamate-$I^{125}$). When renal excretory function is impaired, either acutely or chronically, one or more of the GFR determinants is altered unfavorably so that total GFR declines. In this study, GFR was measured by blood turnover rate of iothalamate-$I^{125}$ (J. Lab. Clin. Med., 89:845–856 (1972)), as well as by plasma creatinine and serum urea nitrogen levels. Results are shown in Table 2, and FIG. 1. FIG. 1 shows the effect of DMSA treatment on GFR. The DMSA group is compared to normal controls (CD6) and to animals treated with lead for six months, then sacrificed at twelve months (ED6). As can be seen in FIG. 1, animals given DMSA showed significantly increased GFR, confirmed by lower SUN and serum creatinine levels than those in the animals without DMSA.

TABLE 2

| | GFR (ml/min/100 g) | SERUM CREATININE (mg/dl) | SUN (mg/dl) |
|---|---|---|---|
| C1 | 0.59 ± 0.27 | 0.46 ± 0.04 | 19.3 ± 4.0 |
| C6 | 1.09 ± 0.13 | 1.08 ± 0.14 | 12.8 ± 2.4 |
| CD6 | 0.96 ± 0.05 | 1.59 ± 0.14 | 14.4 ± 2.0 |
| ED6 | 0.82 ±** 0.14 | 1.96 ±** 0.28 | 20.8 ± 7.2 |
| DMSA | 1.16 ±* 0.13 | 1.00 ±* 0.10 | 11.1 ±* 2.2 |

*$P < 0.05$ when compared to ED6 and CD6
**$P < 0.05$ when compared to CD6

Likewise, GFR was also measured for rats given 0.01% (low lead) vs. 0.5% (high lead) lead acetate in their drinking water for six months, followed by administration of distilled water for the next six months (ED6A), and for controls (CD6A). In such discontinuous low lead treated rats which were further treated with DMSA, GFR was significantly increased, as shown in Table 3, similarly to the results shown (in Table 2) for the discontinuous high lead treated rats.

TABLE 3

| | GFR (ml/min/100 g) |
|---|---|
| CD6A | 0.94 ± 0.20 |
| ED6A | 0.88 ± 0.22 |
| DMSA | 1.09 ± 0.19 |

EXAMPLE 3

Blood Pressure Levels

Figure 2:
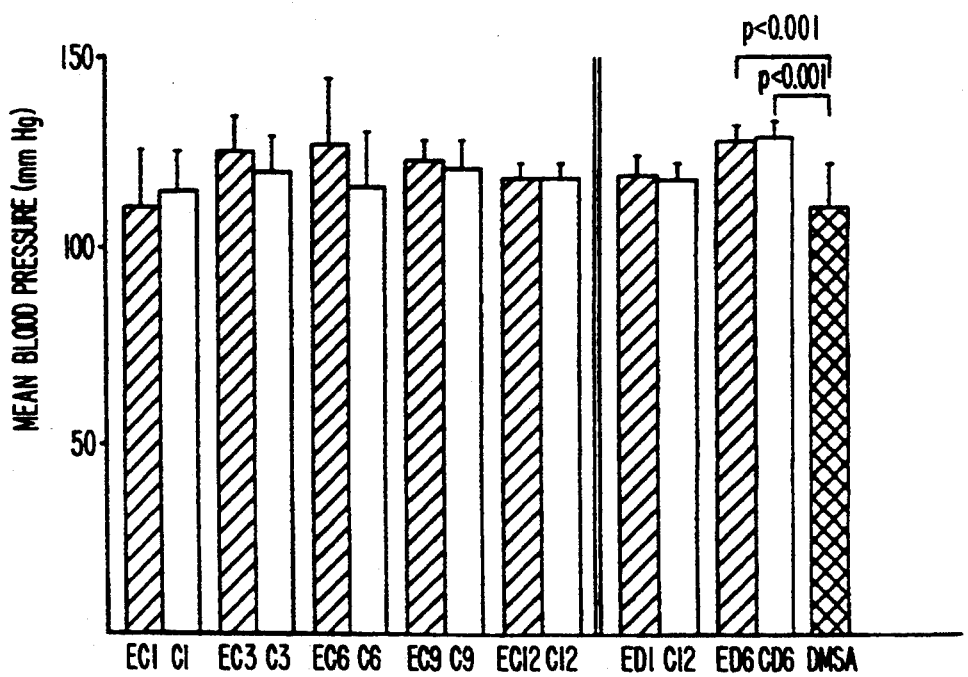
FIG. 2 is a graph showing the effect of DMSA on mean blood pressure.

Mean blood pressure recordings were obtained using an automated tail blood pressure device. Results are shown in FIG. 2. Blood pressure is shown to increase with age in both control animals and lead treated animals. DMSA treatment restored blood pressure to levels seen in young animals (C1), and significantly reduces blood pressure below ED6 and CD6 controls.

EXAMPLE 4

Blood Pressure Levels—Low vs. High Lead Diet

Figure 3:
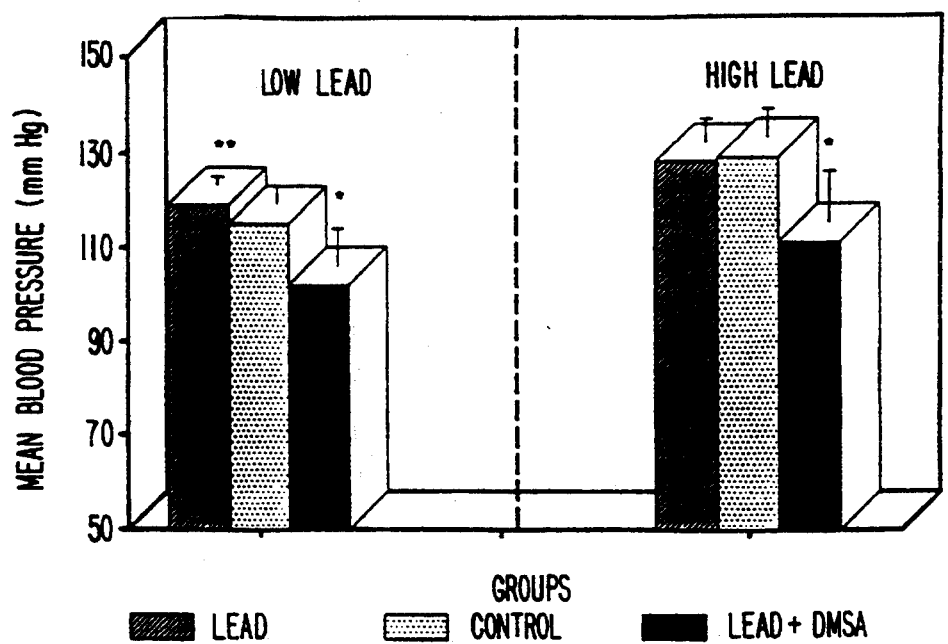
FIG. 3 is a graph showing the effect of administration of DMSA on the blood pressure of both low lead and high lead treated rats.

Four groups of rats were given either 0.01% (low lead) or 0.5% (high lead) lead acetate in their drinking water for six months, followed by administration of distilled water for the next 6 months (discontinuous low lead (ED6A); and discontinuous high lead (ED6)). One of the discontinuous low lead groups and one of the discontinuous high lead groups were given three courses of 0.5% dimercaptosuccinic acid (DMSA) for 5 days, 2 months apart (DMSA-A and DMSA groups, respectively), after lead was discontinued. Both ED6A and ED6 groups had age-matched, pair-fed controls. There was no change in blood pressure of discontinuous high lead-treated rats as compared to controls, but blood pressure of discontinuous low lead-treated rats increased significantly above controls (FIG. 3). Administration of DMSA had a blood pressure lowering effect on both high and low lead-treated rats, which was also significantly below blood pressure of normal rats (FIG. 3).

A recent major thrust of hypertension research has been on humoral vasoactive substances produced by vascular endothelium, which act locally on vascular smooth muscle to produce either vasoconstriction or vasorelaxation. The principal vasoconstrictive substance is endothelin, for which a radio-immunoassay is available. Endothelin has been measured in blood vessels, glomeruli, plasma and urine. Although it is produced locally, there are certain disease states (e.g., hypertensive diabetes) in which plasma levels have been found to be elevated. Endothelin-3 is the dominant species of endothelin in the rat, and endothelin-1 is the dominant species in humans. Endothelin-1 is produced predominantly in blood vessels, while endothelin-3 is also produced by the kidney. Endothelium-derived relaxing factor (EDRF) is an important locally-produced vasorelaxant, which has been identified as nitric oxide. As nitric oxide is a very short-lived compound, much of the work which has explored the role of EDRF in hypertension has focussed on measurements of plasma and/or urine cyclic guanosine monophosphate (cGMP), which is a messenger system affected by EDRF.

EXAMPLE 5

Plasma and Urinary cGMP

Accordingly, plasma and urine cGMP were measured as an indirect reflection of EDRF activity in lead-treated rats, and to assess the effect of administration of DMSA on EDRF activity.

Figure 4:
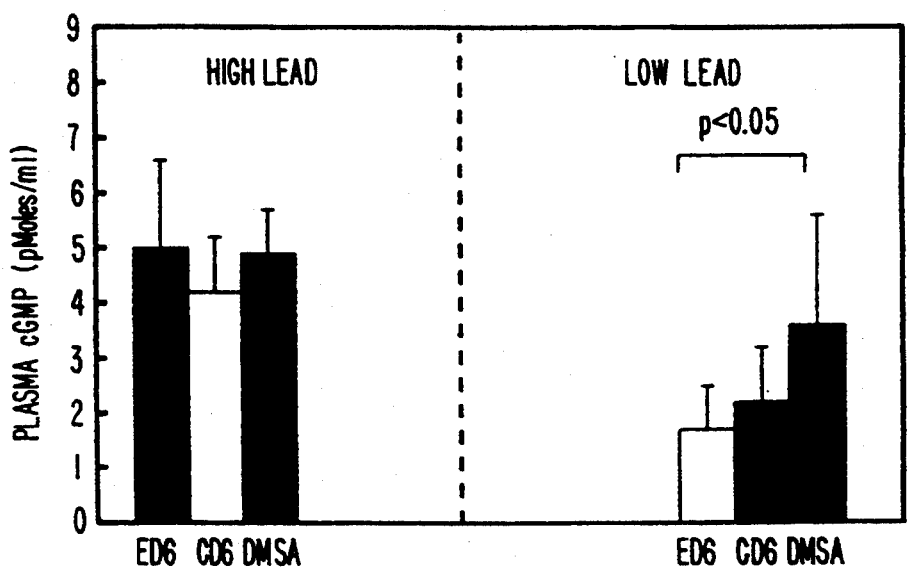
FIG. 4 is a graph showing the effect of administration of DMSA on plasma cGMP levels of low lead treated rats.
Figure 5:
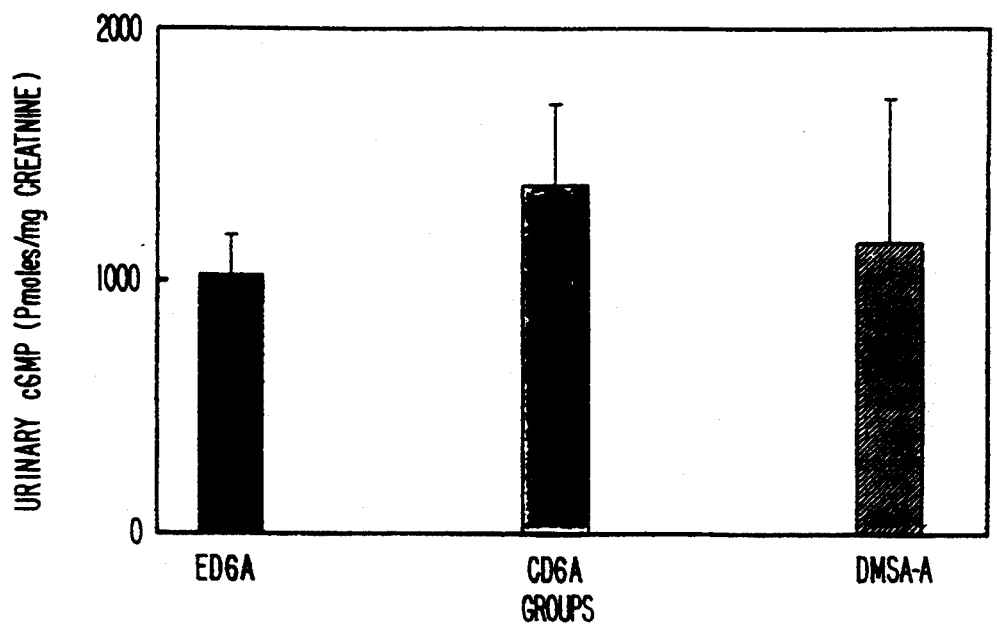
FIG. 5 is a graph showing the effect of administration of DMSA on urinary cGMP levels of low lead treated rats.

Plasma cGMP was significantly lowered in animals treated with high doses of lead for 12 months, and plasma cGMP levels were decreased in low lead-treated rats after both 3 and 12 months as compared to control groups. Urine cGMP levels in low lead-treated rats also showed a decrease when compared to controls. In discontinuous lead-treated rats, plasma cGMP was not affected in either high or low lead-treated groups (FIG. 4), and urinary cGMP in the discontinuous low lead-treated rats was similarly unaffected (FIG. 5). However, treatment of low lead-treated rats with DMSA (administered as in Example 4) resulted in significantly increased plasma cGMP levels (FIG. 4). In contrast, urinary cGMP in low lead-treated rats likewise given DMSA did not increase (FIG. 5).

EXAMPLE 6

Determination of ANF in Rat Plasma

Plasma atrial natriuretic factor (ANF) is another major hormone system which operates via cGMP as a messenger. Accordingly, plasma levels of ANF were measured using a Peninsula Radioimmunoassay Kit. Results are shown in Table 4.

TABLE 4

| Determination of ANF in Rat Plasma by Peninsula Radioimmunoassay Kit | |
|---|---|
| Groups (n = 7) | ANF (pico g/ml) |
| ED6A | 52.8 ± 6.7 |
| CD6A | 49.9 ± 4.8 |
| DMSA-A | 51.5 ± 8.9 |

The ED6A and DMSA-A rats were given 0.01% lead acetate in the drinking water for 6 months, then no lead in the drinking water before being sacrificed at 12 months. As Table 4 indicates, there were no significant differences in the plasma ANF levels measured in the ED6A, CD6A and DMSA-A treated rats. The observation that plasma ANF was unaltered by lead or DMSA supports the interpretation that the cGMP changes shown in FIG. 4 were related to an EDRF effect.

EXAMPLE 7

Plasma Endothelin

Figure 6:
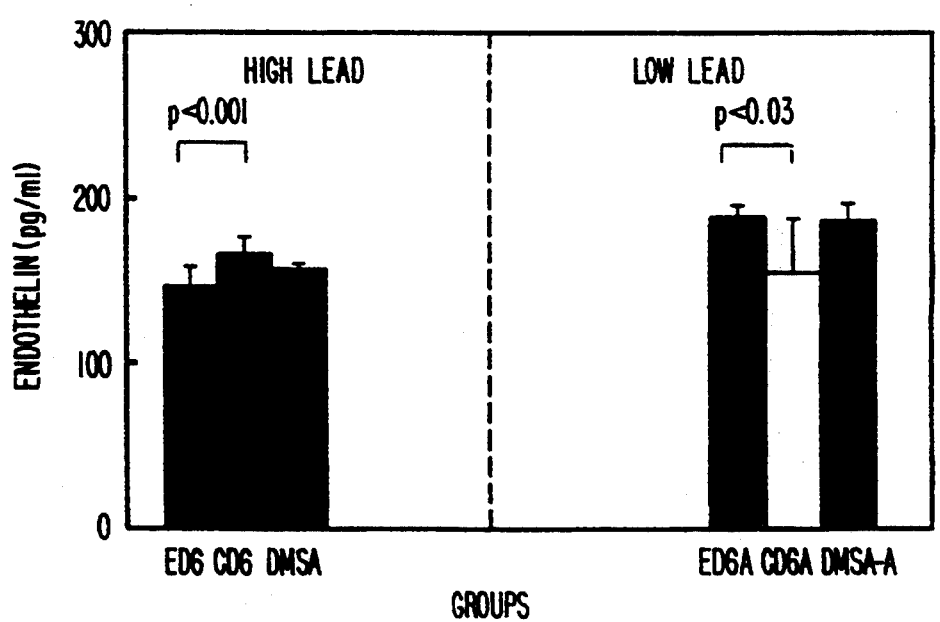
FIG. 6 is a graph showing the effect of administration of DMSA on endothelin-3 concentration in low lead treated rats.

Plasma endothelin-3 concentration was decreased significantly only after 12 months of high lead feeding of rats, and in low lead-treated animals, endothelin-3 was initially increased after 3 months of lead administration but subsequently decreased significantly after 12 months of lead administration. Plasma endothelin-3 in discontinuous high lead-treated (ED6) rats was significantly below controls; however, when plasma from discontinuous low lead-treated rats (ED6A) was examined, plasma endothelin-3 concentration was significantly increased when compared with control rats (FIG. 6). DMSA administration (administered as in Example 4) had no effect on plasma endothelin-3 concentration (FIG. 6).

EXAMPLE 8

Kidney cGMP

Figure 7:
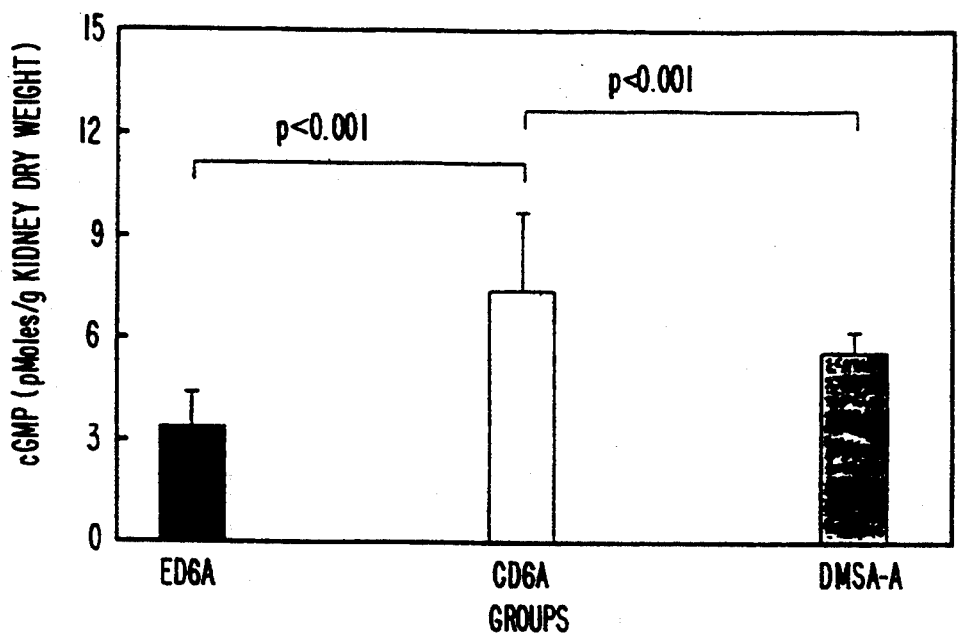
FIG. 7 is a graph showing the effect of administration of DMSA on cGMP levels in kidney glomeruli of low lead treated rats.

Cyclic GMP concentration in glomeruli of rats treated continuously with high doses of lead from 1 to 12 months was generally decreased as compared to controls, but never reaching a significant level, and similar results were observed for rats treated continuously with low doses of lead. However, glomeruli from discontinuous low lead treated rats had decreased cGMP levels as compared to controls, which increased with DMSA treatment (FIG. 7).

EXAMPLE 9

Kidney Endothelin

Figure 8:
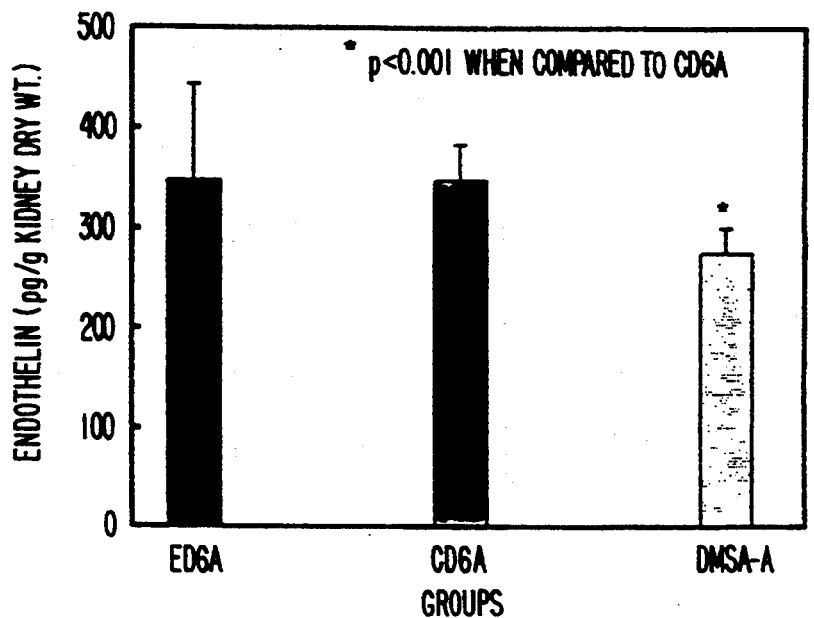
FIG. 8 is a graph showing the effect of administration of DMSA on endothelin-3 concentration in kidney glomeruli of low lead treated rats.

Concentration of endothelin-3 in glomeruli of lead-treated rats was increased significantly after three months of high lead feeding, when compared to controls. There was no change in concentration of glomerular endothelin-3 in high lead rats after 12 months. In low lead rats, glomerular endothelin-3 concentration decreased after 12 months of lead administration, as compared to control, but was unchanged at three months (in contrast to the increased plasma endothelin-3 level observed at three months). In discontinuous low lead treated rats, glomerular concentration of endothelin-3 was not altered when compared to controls (FIG. 8). DMSA (administered as in Example 4), however, lowered the concentration of endothelin-3 in glomeruli from low lead-treated rats (FIG. 8).

EXAMPLE 10

Kidney Lead and Silicon

Figure 9:
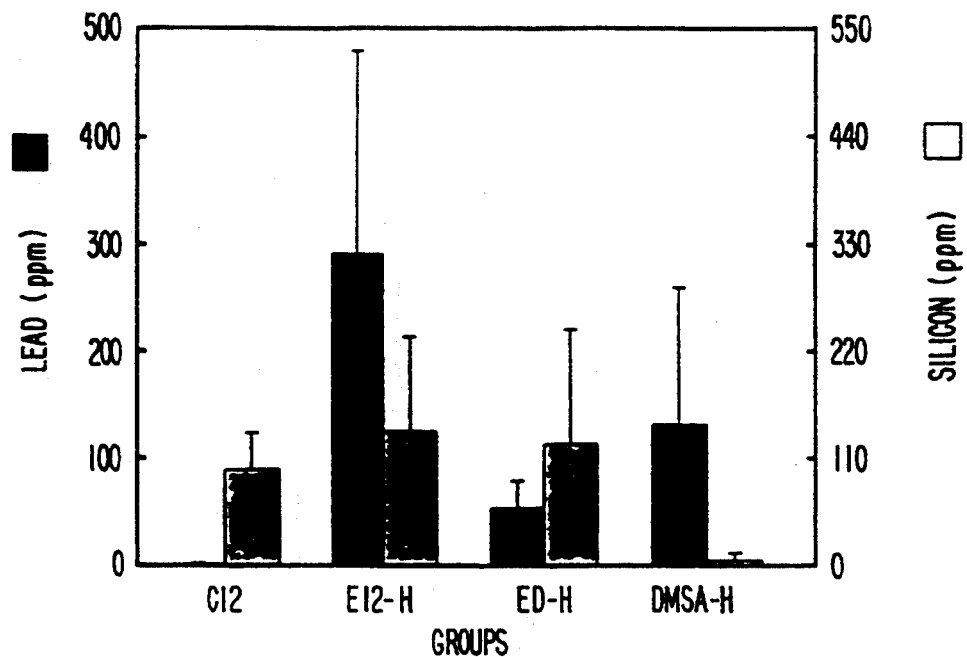
FIG. 9 is a graph showing the effect of administration of DMSA on kidney silicon levels in high lead treated rats.

The silicon and lead contents of kidney cortex in high dose lead-treated rats are displayed in FIG. 9. Discontinuation of lead (ED-H) resulted in a marked fall in lead content, with less change in silicon, whereas DMSA treatment (as described in Example 4) resulted in a much greater reduction in silicon content than lead.

EXAMPLE 11

Kidney Reactive Oxygen Metabolites

Figure 10:
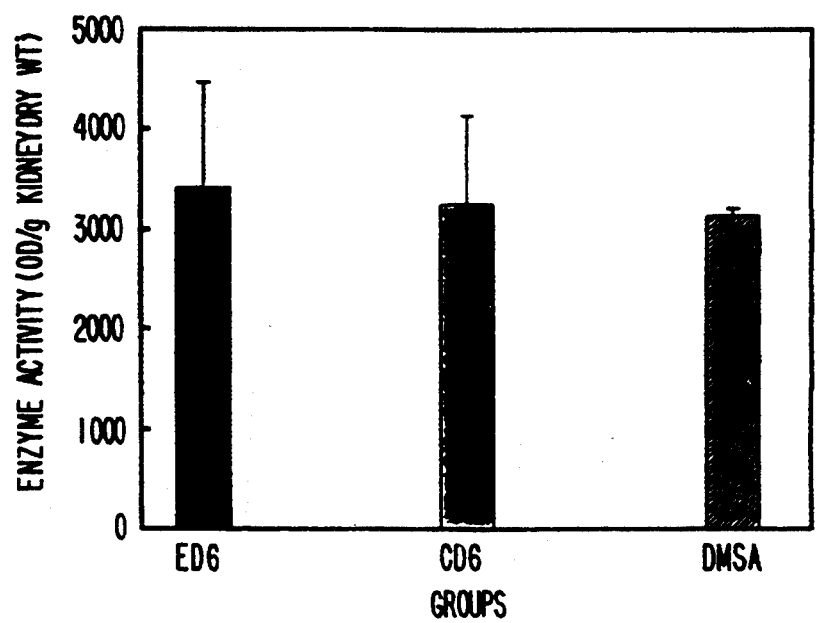
FIG. 10 is a graph showing the effect of administration of DMSA on kidney metalloproteinase activity in high lead treated rats.

The presence of reactive oxygen metabolites was assessed indirectly by measurement of metalloproteinase enzymes in kidneys of lead-treated rats. An increase in metalloproteinase is believed to reflect an increased accumulation of reactive oxygen metabolites. In both high and low dose lead-treated rats, metalloproteinase activities were increased significantly after 12 months of lead administration, but no alteration in their activity was observed at three months. There was no change in activities of these enzymes in either discontinuous high dose lead-treated, or DMSA-treated, rats (FIG. 10).

As referenced previously, silicon has been demonstrated to act as an inhibitor of the enzyme superoxide dismutase, which would be expected to result in accumulation of superoxide anions. However, neither the activity of superoxide dismutase, nor the level of superoxide anions, were measured directly in this experiment. The absence of a change in glomerular metalloproteinases after DMSA does not of necessity negate the conclusion that superoxide anion concentration was decreased, as the metalloproteinases reflect total reactive oxygen species accumulation, and a change in only one species may be masked. Furthermore, the increase in glomerular cGMP after administration of DMSA (FIG. 7) can be explained by a decrease in superoxide anions, which have been demonstrated to inactivate EDRF.

EXAMPLE 12

Effect of DMSA Administration on Normal Young Rats Fed High silicon and Low Silicon Diets Male Sprague-Dawley rats were fed a semi-purified diet which either contained sodium metasilicate (silicon=500 ppm; groups S3G3 and S4G4) or no silicon (S1G1 and S2G2) (silicon content of the basic diet was very low at 5 ppm). Sodium chloride was added to the diet of the rats that received no silicon to produce an equivalent sodium content to the diets that contained sodium metasilicate. All rats were given the appropriate diets for three months. Half of the rats from each group were also given three 5-day courses of 0.5% DMSA at one-month intervals starting after they had received their appropriate diets for one month (high Si=S3G3; low Si=S1G1).

Figure 11:
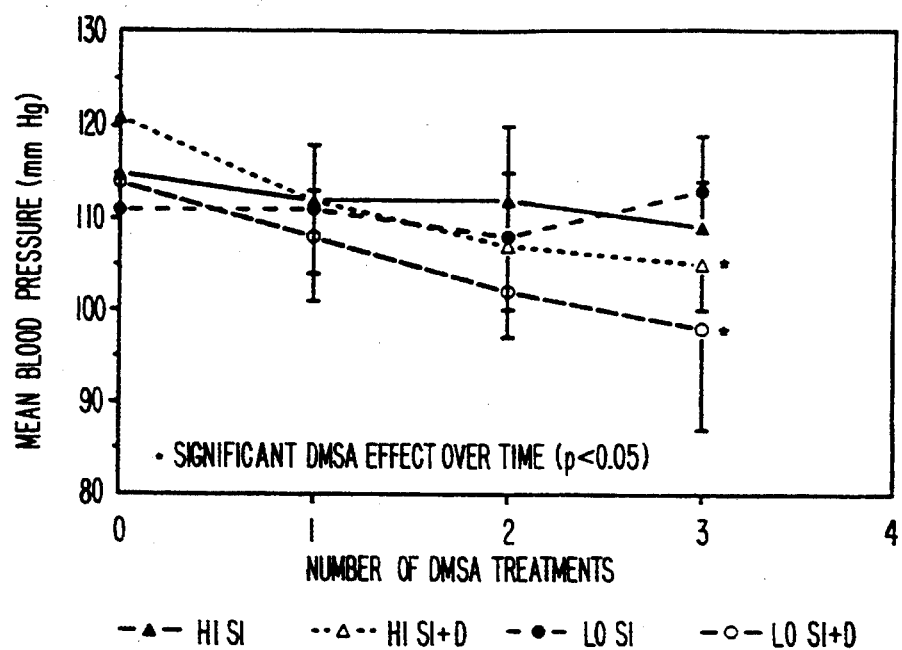
FIG. 11 is a graph showing the effect of repeated treatments of DMSA on blood pressure in rats fed both high and low silicon diets.

There was no change in glomerular filtration rate (GFR) among all four groups (see Table 6, below). There was no change in blood pressure of rats treated with either high silicon (low chloride) or low silicon (high chloride) diets. However, treatment with DMSA resulted in a significant decrease in blood pressure of both groups (FIG. 11).

Figure 12:
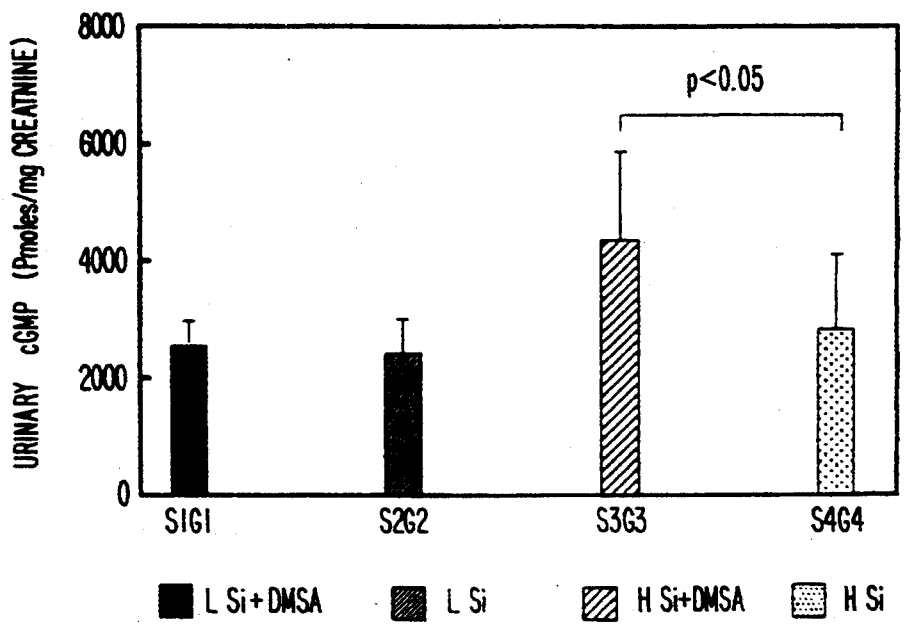
FIG. 12 is a graph showing the effect of administration of DMSA on urinary cGMP concentrations in normal rats fed low and high silicon diets.
Figure 13:
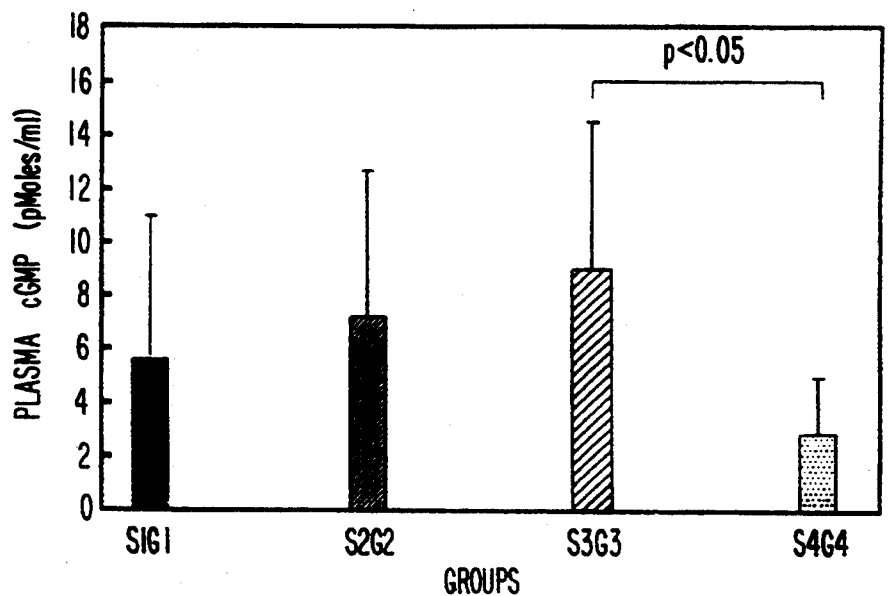
FIG. 13 is a graph showing the effect of administration of DMSA on plasma cGMP concentrations in normal rats fed low and high silicon diets.

Urinary and plasma cGMP, as indirect measures of EDRF, were also measured in all four groups. There was no change in either urinary or plasma cGMP of rats given low silicon with or without DMSA administration (FIGS. 12 and 13). However, there was significant elevation of urinary and plasma cyclic GMP in groups of rats fed high silicon diet and treated with DMSA, as compared to the rats given high silicon diet alone (FIGS. 12 and 13).

Figure 14:
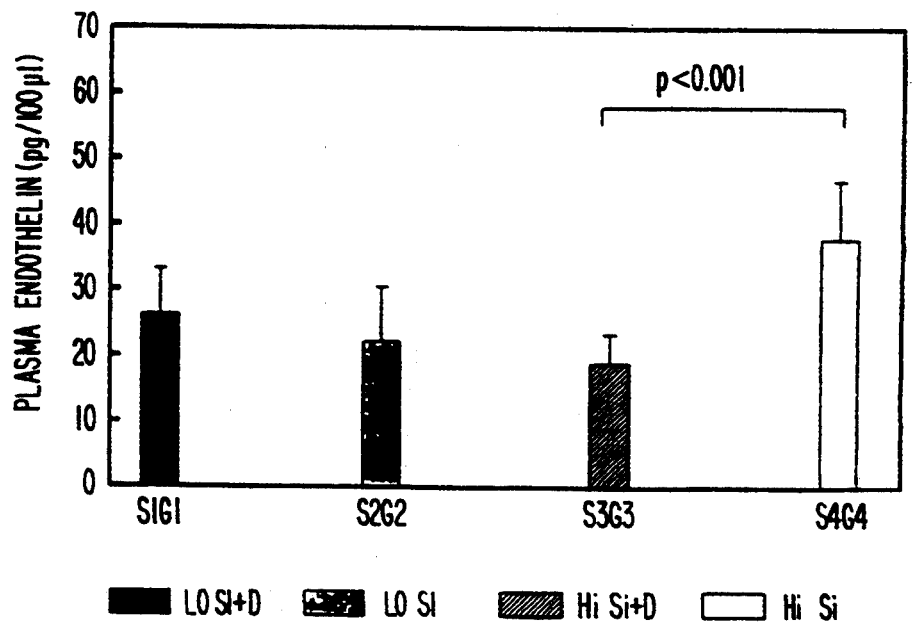
FIG. 14 is a graph showing the effect of administration of DMSA on plasma endothelin levels in normal rats fed low and high silicon diets.

There was no difference in plasma endothelin concentration of rats fed low silicon, with or without DMSA-treatment (FIG. 14). Rats given high silicon diet (S4G4) had higher plasma endothelin levels than rats on low silicon diet (S2G2), and plasma endothelin was lowered significantly with DMSA treatment (S3G3) (FIG. 14).

Figure 15:
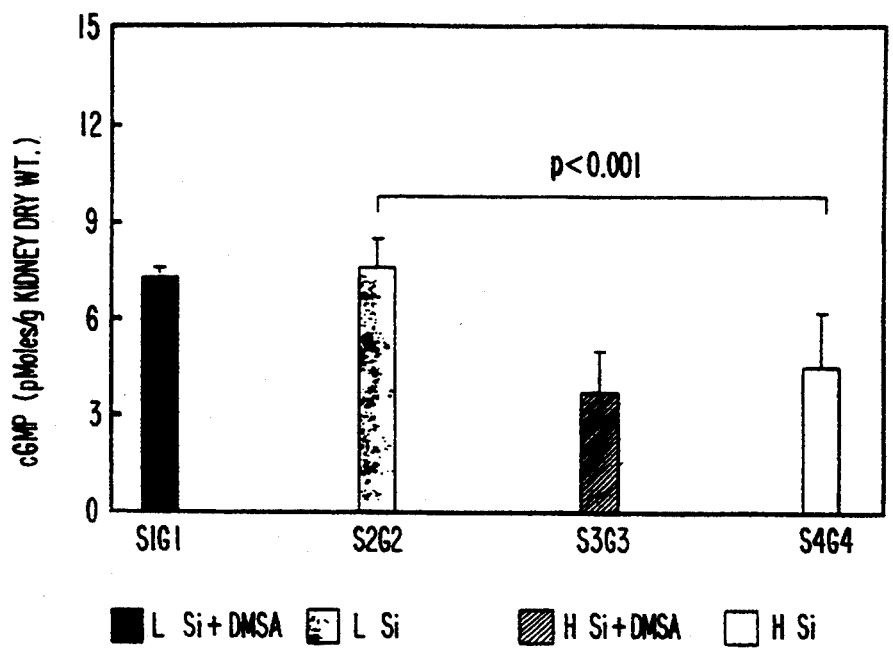
FIG. 15 is a graph showing the effect of administration of DMSA on kidney glomeruli cGMP concentration in normal rats fed low and high silicon diets.

Cyclic GMP concentration in glomeruli decreased significantly in rats given high silicon diet (S4G4) as compared to low silicon rats (S2G2) (FIG. 15), which might be anticipated from the effect of silicon on superoxide dismutase activity. However, treatment with DMSA did not cause a change in concentration of glomerular cGMP in either group (FIG. 15).

Figure 16:
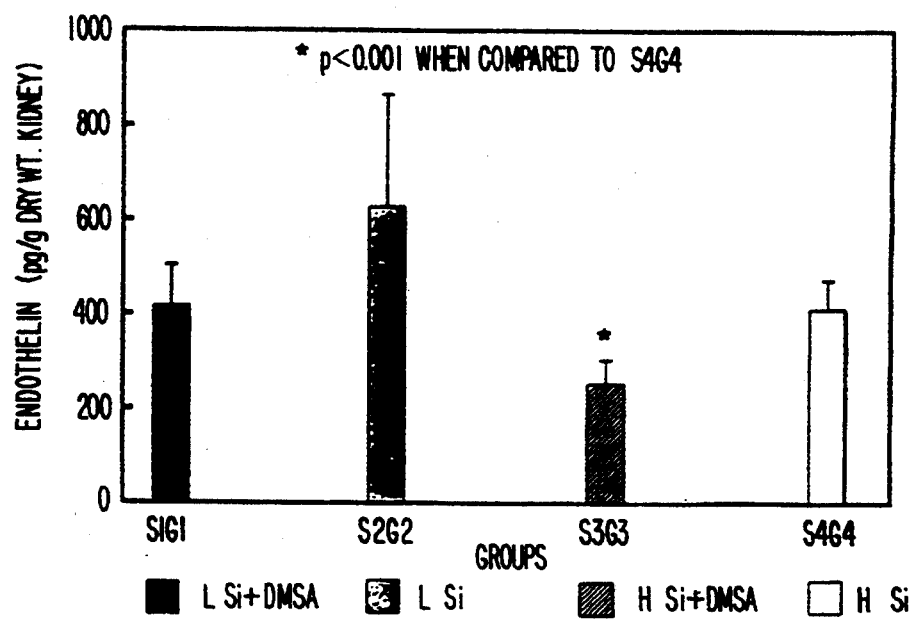
FIG. 16 is a graph showing the effect of administration of DMSA on kidney glomeruli endothelin-3 concentrations in normal rats fed low and high silicon diets.

Glomerular endothelin-3 was reduced significantly in rats fed high silicon diet and then treated with DMSA (FIG. 16). There was no change in glomerular endothelin-3 concentration in rats given low silicon diet (FIG. 16).

Figure 17:
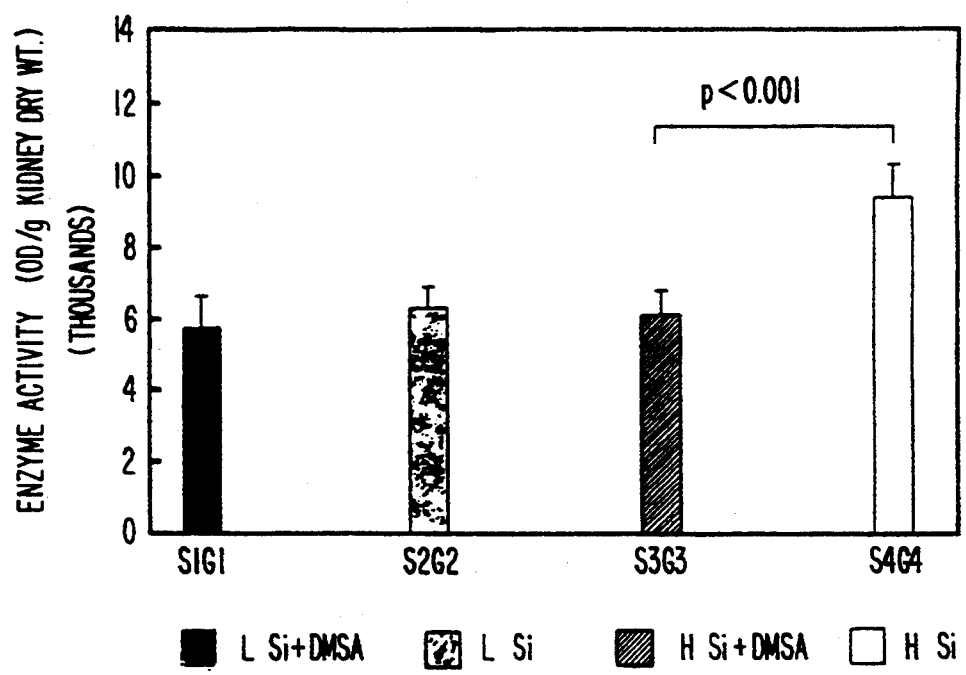
FIG. 17 is a graph showing the effect of administration of DMSA on kidney glomeruli metalloproteinase activity in normal rats fed low and high silicon diets.
Figure 18:
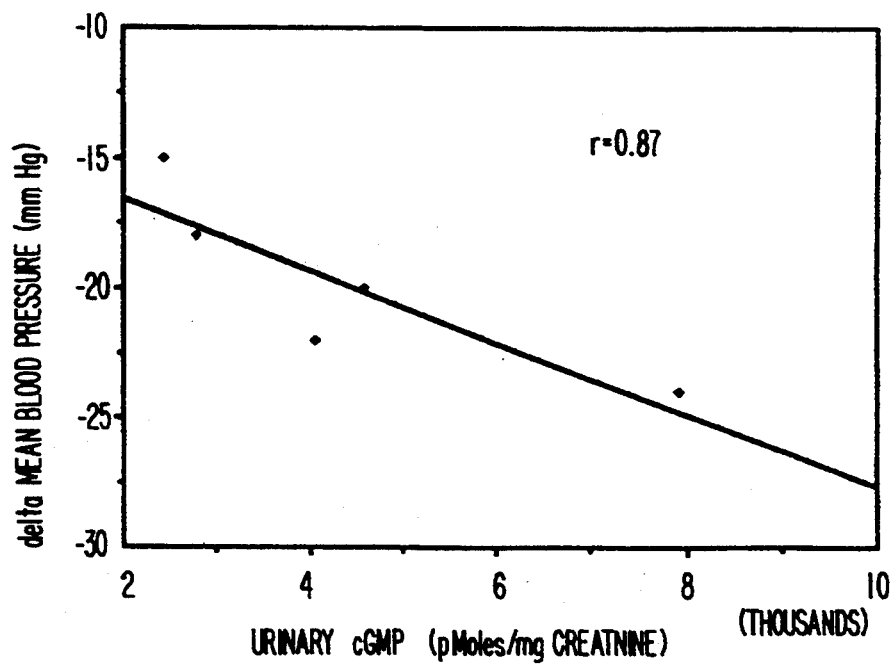
FIG. 18 is a graph showing the correlation between the change in blood pressure and the urinary cGMP in normal rats.
Figure 19:
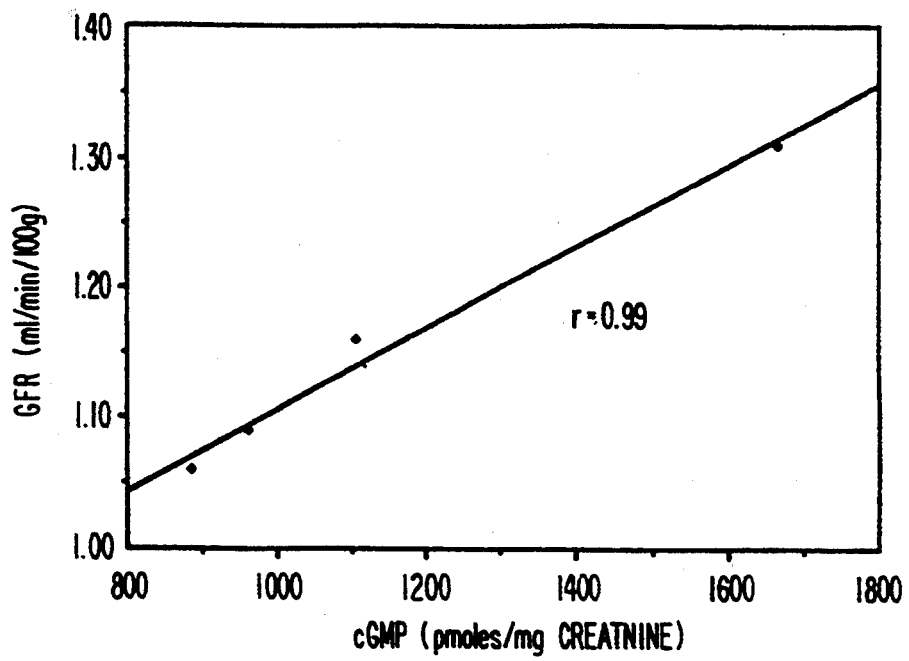
FIG. 19 is a graph showing the correlation between the GFR and cGMP levels in lead and DMSA treated rats.

FIG. 17 shows metalloproteinase activity in glomeruli. As shown, high silicon diet appears to increase the activity of glomerular metalloproteinase, which is lowered subsequently with DMSA treatment, again consistent with a silicon effect on superoxide dismutase.

EXAMPLE 13

Effect of DMSA Administration on Normal Aged Rats Given High and Low Silicon Diets Male Sprague-Dawley rats, aged 2 months, were fed either low or high silicon diet for 13 months. In these animals, sodium was supplemented in the diet of the low silicon group as sodium acetate rather than sodium chloride. Half of the rats from each group were given three 5-day courses of DMSA at one month intervals, starting after they had received appropriate diets for eleven months.

Figure 20:
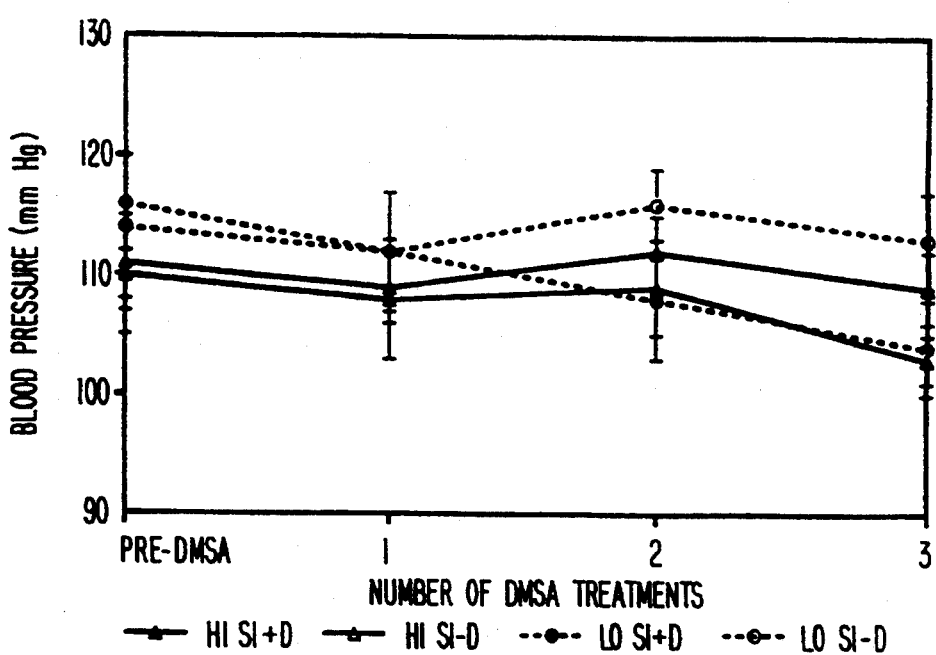
FIG. 20 is a graph showing the effect of administration of DMSA on blood pressure of normal aged rats fed high and low silicon diets.

There was no change in GFR among all four groups (Table 5 below). Blood pressures of rats treated with DMSA were significantly lowered (FIG. 20). The blood pressure values for aged animals treated with DMSA were similar to the blood pressure values seen for young rats (FIG. 11). The GFR in these aged animals was significantly lower than previously observed in our 9-months control animals (0.60±0.15 vs. 0.98±0.19), confirming the predicted effect of aging on GFR.

TABLE 5

| Group | Aged Normal Rats GFR (ml/min/100 g) |
|---|---|
| High Si + DMSA | 0.64 ± 0.11 |
| High Si | 0.60 ± 0.16 |

TABLE 5-continued

| Group | Aged Normal Rats GFR (ml/min/100 g) |
|---|---|
| Low Si + DMSA | 0.58 ± 0.14 |
| Low Si | 0.62 ± 0.14 |

EXAMPLE 14

Effect of DMSA Administration on Uremic Rats Fed Either High or Low Silicon Diets Male Sprague-Dawley rats were made uremic by ligating renal arteries to the left kidney and removing the right kidney. The 5/6 nephrectomized rats were then fed either low or high silicon diet for 3 months. Sodium was supplemented in the low silicon diet as sodium chloride. Half of the rats from each silicon group were given two 5-day courses of 0.2% DMSA at one month intervals, starting after they had received appropriate diets for one month.

Figure 21:
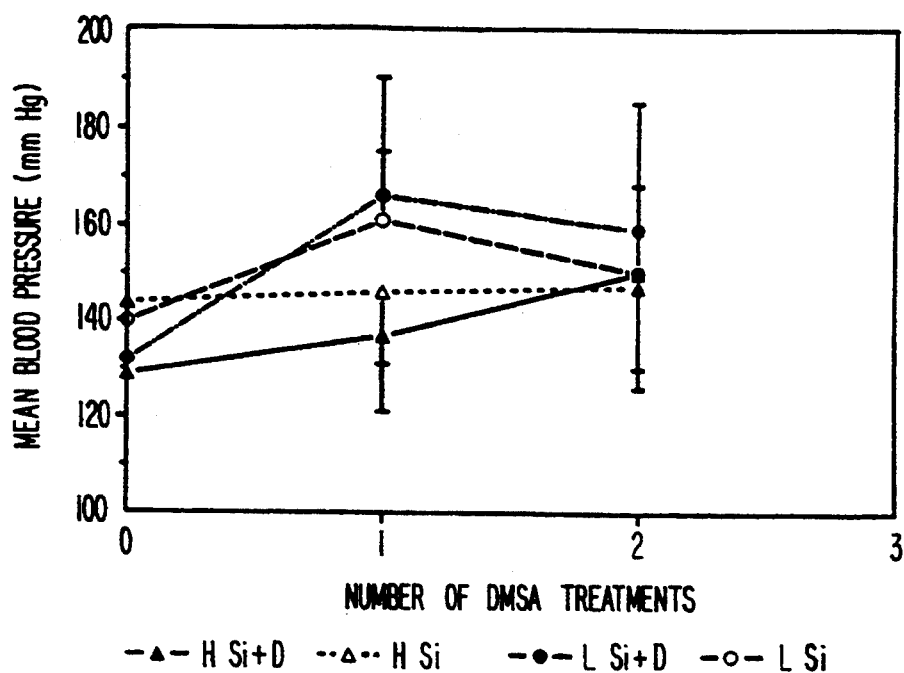
FIG. 21 is a graph showing the effect of administration of DMSA on blood pressure of nephrectomized rats fed high and low silicon diets.

Table 6 and FIG. 21 show GFR and blood pressure changes in 5/6 nephrectomized rats, respectively. Neither high silicon diet nor DMSA treatment had an effect on GFR or blood pressure of 5/6 nephrectomized rats, as compared to the DMSA effect in normal controls or lead-treated animals. All kidneys showed severe glomerulosclerosis and tubulo-interstitial disease.

TABLE 6

| | GFR (ml/min/100 g) | | |
|---|---|---|---|
| | 5/6 Nephrectomized | Glomerulonephritic | Young Controls |
| low silicon + DMSA | 0.30 ± 0.13 | 0.78 ± 0.17 | 0.85 ± 0.18 |
| low silicon | 0.25 ± 0.13 | 0.77 ± 0.07 | 0.84 ± 0.17 |
| high silicon + DMSA | 0.30 ± 0.15 | 0.78 ± 0.12 | 0.87 ± 0.07 |
| high silicon | 0.25 ± 0.05 | 0.79 ± 0.18 | 0.85 ± 0.17 |

EXAMPLE 15

Effect of DMSA on Glomerulonephritic Rats Given High or Low Silicon Diets

Another group of rats were also made mildly uremic with injections of rabbit anti-rat glomerular basement membrane antibody. The mildly uremic rats were fed low or high silicon diets, and the low silicon diet was supplemented with sodium chloride to maintain constant sodium intake. Half of the rats from each diet group were given three 5-day courses of 0.5% DMSA at one month intervals, starting after one month of treatment with appropriate diets.

Figure 22:
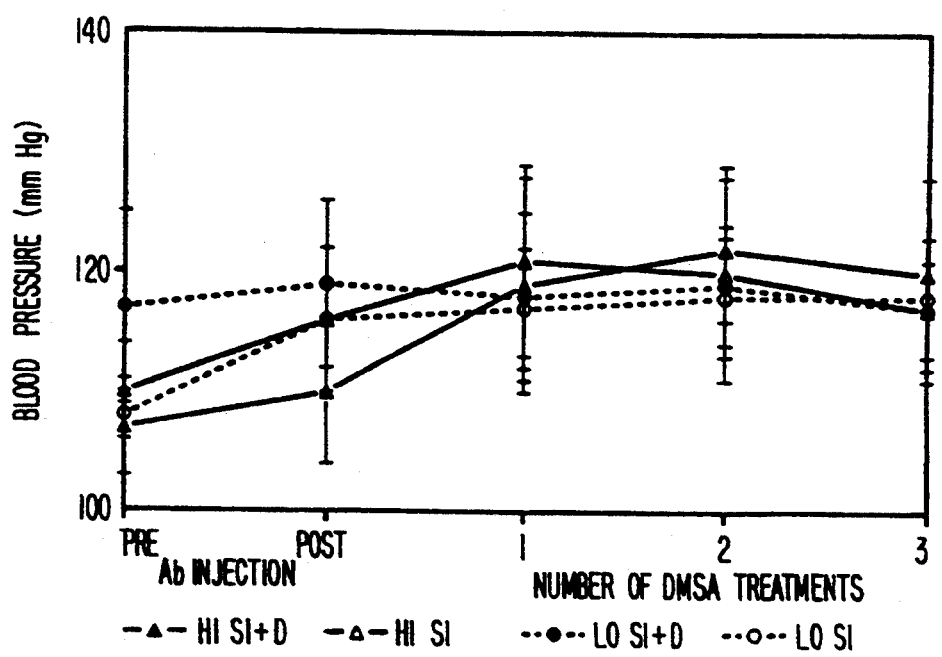
FIG. 22 is a graph showing the effect of administration of DMSA on blood pressure of glomerulonephritic rats fed high and low silicon diets.

Table 6 and FIG. 22 show changes in GFR and blood pressure of glomerulonephritic rats. Blood pressure and GFR were not affected by either silicon feeding or DMSA treatment in glomerulonephritic rats, as compared to their normal controls. Kidneys examined by light and electron microscopy showed a mild glomerulonephritis with linear deposition of electron dense material in glomerular basement membranes. DMSA has no effect on the pathologic changes or on total urinary protein excretion.

The above results show that low dose lead administration increases plasma endothelin-3 and decreases plasma and urinary cGMP as a presumed reflection of decreased EDRF effect. As lead may increase the production of free oxygen radicals, and as the superoxide anion, in particular, has been shown to inactivate EDRF, the low lead effect on EDRF may be exerted by this mechanism. Alternatively, elevation of tissue silicon levels, as a secondary result of lead administration, may inhibit superoxide dismutase. Finally, EDRF may be reduced through the feedback interrelationship with endothelin.

Endothelin not only has a direct effect on increasing vascular smooth muscle intracellular calcium, but also directly stimulates norepinephrine and aldosterone production and leads to venous as well as arterial constriction. The central volume expansion due to the aldosterone-mediated retention of $Na^+$ and to venous constriction stimulates the release of the Na-K-ATPase inhibiting natriuretic hormone, which also has an effect on vascular smooth muscle membrane transport, resulting in increased intracellular calcium. The final result is increased vasoconstriction and hypertension. DMSA appears to have a beneficial effect by increasing EDRF and decreasing endothelin-3 in the lead-treated rats. Those humoral changes result not only in improved blood pressure but also in improved GFR. DMSA also has a beneficial effect on blood pressure of young normal animals, aged normal animals, and an ameliorating effect on blood pressure of 5/6 nephrectomized and glomerulonephritic rats. However in contrast to the beneficial effect of DMSA on GFR in lead-treated rats, DMSA had no effect on GFR (or on renal pathology) in these four groups of animals.

EXAMPLE 16

Effect of DMSA on Clearance of Silicon and Aluminum in Human Dialysis Patients

Four patients have been studied, each at two different doses of DMSA (5 mg/kg and 10 mg/kg in the first patient, and 10 mg/kg and 20 mg/kg in the remaining patients).

DMSA significantly increased silicon clearance, with the maximum effect observed during the dialysis following the day of DMSA administration (DMSA was given early Wednesday A.M. and clearances were measured Wednesday P.M. and Friday P.M.). Relatively little effect was observed on aluminum clearance.

In a separate component of this study, plasma (arterial and venous) silicon was measured before and after dialysis in 30 unselected patients. Silicon clearances were also calculated. These patients had silicon values ranging from slightly above normal to 6× normal.

EXAMPLE 17

Determination of Vascular Reactivity

Measurement of the amount of contraction caused by a vasoconstrictor in the presence of a compound under study provides an effective indicator of vascular reactivity. A reduction in vascular reactivity would indicate a relaxation of the vascular smooth muscle. (*American J. Hypertension* 2:754 (1989); *American Physiological Society* H211 (1981)). Vascular reactivity was measured by looking at the dose-contraction response to norepinephrine in isolated arteries of low lead and control animals: CD6A (control), ED6A (discontinuous low lead), and DMSA-A (discontinuous low lead +DMSA). No significant change in vascular reactivity among the three groups was measured, indicating that the DMSA effect on blood pressure does not result from a direct reduction in vascular reactivity.

EXAMPLE 18

Detection of HAP

Rats treated with low dose lead (0.01% lead acetate) in the drinking water developed hypertension by the third month of feeding. The hypertension persisted throughout 12 months of continuous feeding but was also seen in rats administered lead for 6 months, then for the next 6 months given normal drinking water (ED6A). SDS gels using marker proteins of molecular weights 8.2 kilodaltons (kD), 14.6 kD, and 17.2 kD of the plasma from ED6A, CD6A, young normal controls (C1A), and DMSA-A were run. Plasma from a ED6A rat showed an intense band at 12 kD and the plasma from a CD6A (aged normal control) rat showed a less intense band at 12 kD. Significantly, the plasma from a C1A rat and from a lead-treated rat given 3 courses of DMSA (DMSA-A) showed a virtual absence of the 12 kD band. This band is thought to be the hypertension associated protein (HAP). Thus, DMSA reduces the concentration of the HAP band to levels seen only in young normal rats. This effect was seen 2 months after the last dose of DMSA. Therefore, these results reflect either a suppression of synthesis of HAP or an increased breakdown of HAP.

Since silicon levels are known to be significantly elevated in Alzheimer's disease in the neurofibrillary tangles, and since there is a known diffuse increase in silicon levels in the brain in cases of senile dementia, the reduction of silicon levels through administration of DMSA can be expected to improve the condition of patients exhibiting the symptoms of Alzheimer's disease and/or senile dementia, or to prevent onset of such diseases.

While embodiments and applications of this invention have been shown and described, it would be apparent to those skilled in the art that other and further embodiments of the invention are possible without departing from the inventive concepts herein, and such other embodiments are believed to be within the scope of the invention. The invention, therefore, is not to be restricted except in the spirit of the appended claims.

We claim:

1. A method for reducing blood pressure in a human or other animal, comprising administering to said human or other animal an effective amount of dimercaptosuccinic acid.

2. The method of claim 1 wherein said amount of dimercaptosuccinic acid is effective to reduce silicon levels in the blood or tissue of said human or other animal.

3. The method of claim 1 wherein said amount of dimercaptosuccinic acid is effective to decrease accumulation of reactive oxygen metabolites in said human or other animal.

4. The method of claim 3 wherein said accumulation of reactive oxygen metabolites is decreased through increased superoxide dismutase activity.

5. The method of claim 1 wherein said amount of dimercaptosuccinic acid is effective to increase cyclic GMP levels in said human or other animal.

6. The method of claim 1 wherein said amount of dimercaptosuccinic acid is effective to decrease endothelin levels in said human or other animal.

7. The method of claim 1 wherein said amount of dimercaptosuccinic acid is effective to increase levels of endothelium-derived relaxing factor in said human or other animal.

* * * * *